United States Patent [19]

Ng

[11] Patent Number: 5,100,387

[45] Date of Patent: * Mar. 31, 1992

[54] DISPOSABLE UNIVERSAL NEEDLE GUIDE APPARATUS (FOR AMNIOCENTESIS)

[76] Inventor: Raymond C. Ng, 1737 Oak Grove, San Marino, Calif. 91108

[*] Notice: The portion of the term of this patent subsequent to Dec. 3, 2008 has been disclaimed.

[21] Appl. No.: 554,382

[22] Filed: Jul. 19, 1990

Related U.S. Application Data

[63] Continuation-in-part of Ser. No. 546,896, Jul. 2, 1990, Pat. No. 5,069,665.

[51] Int. Cl.⁵ .............................................. A61M 5/00
[52] U.S. Cl. ....................................... 604/116; 604/51; 604/272; 128/765
[58] Field of Search .................. 604/116, 117, 35, 51, 604/93, 272, 164; 606/108, 172; 128/765, 662.05, 763

[56] References Cited

U.S. PATENT DOCUMENTS

| | | | |
|---|---|---|---|
| 1,215,512 | 2/1917 | Fetzer | 27/24.1 |
| 2,032,723 | 3/1936 | Schweser | 604/183 |
| 2,338,800 | 1/1944 | Burke | 604/117 |
| 2,451,183 | 10/1948 | Tantimonaco | 604/115 |
| 2,922,420 | 1/1960 | Cheng | 604/272 |
| 2,952,256 | 9/1960 | Meader et al. | 604/272 |
| 3,630,198 | 12/1971 | Henkin | 604/170 |
| 3,896,810 | 7/1975 | Akiyama | 604/117 |
| 3,961,622 | 6/1976 | Edwards | 128/763 |
| 4,020,835 | 5/1977 | Nordstrom et al. | 604/168 |
| 4,058,114 | 11/1977 | Soldner | 128/662.05 |
| 4,280,508 | 7/1981 | Barrada | 128/736 |
| 4,346,717 | 8/1982 | Haerten | 128/662.05 |
| 4,402,324 | 9/1983 | Lindgren et al. | 128/662.05 |
| 4,407,294 | 10/1983 | Vilkomerson | 128/662.05 |
| 4,490,139 | 12/1984 | Huizenga et al. | 604/57 |
| 4,565,545 | 1/1986 | Suzuki | 604/164 |
| 4,608,989 | 9/1986 | Drue | 128/662.05 |
| 4,633,863 | 1/1987 | Filips et al. | 128/846 |
| 4,721,506 | 1/1988 | Teves | 604/51 |
| 4,723,544 | 2/1988 | Moore et al. | 604/116 |
| 4,733,661 | 3/1988 | Palestrant | 606/108 |
| 4,760,847 | 8/1988 | Vaillancourt | 606/185 |
| 4,834,722 | 5/1989 | Zenz | 604/272 |
| 4,850,975 | 7/1989 | Furukawa | 604/170 |
| 4,883,053 | 11/1989 | Simon | 604/116 |

OTHER PUBLICATIONS

Jiri Sonek, M.D., "Articulated Needle Guide: Report on the First 30 Cases", vol. 74, No. 5, Nov. 1989, Obstetrics & Gynecology.

Primary Examiner—Gene Mancene
Assistant Examiner—Michael Lynch
Attorney, Agent, or Firm—William W. Haefliger

[57] ABSTRACT

A surgical needle guide apparatus comprising a substantially horizontal base to be applied to a surface on or adjacent a patient's body surface zone to be punctured by the needle; an upright guide flange mounted on the base, there being pivot structure associated with the flange and base and projecting beyond the base, to overhang an open zone adjacent the surface and offset from the flange; and elongated, tubular guide structure having a lower end portion carried by the pivot structure to be manually pivoted so that the needle structure swings adjacent the guide flange, the tubular structure adapted to receive needle structure for guiding movement thereof toward the open zone and at an angle determined by selective swinging of the tubular guide structure relative to the base.

20 Claims, 4 Drawing Sheets

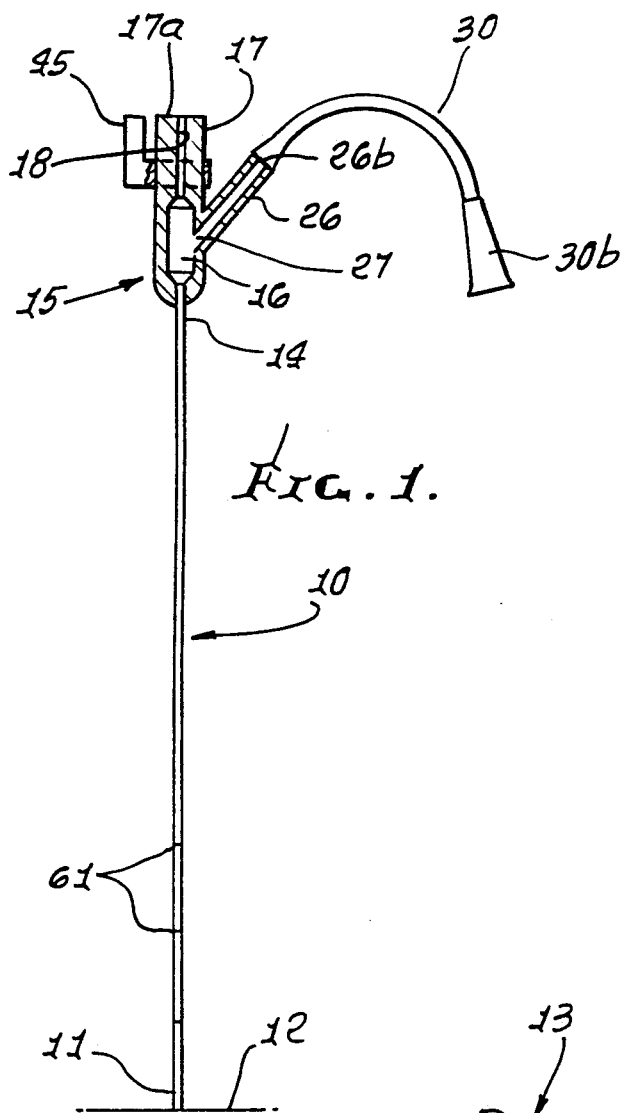
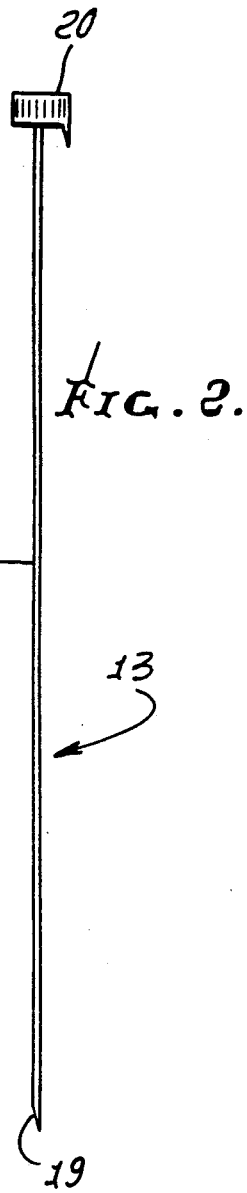
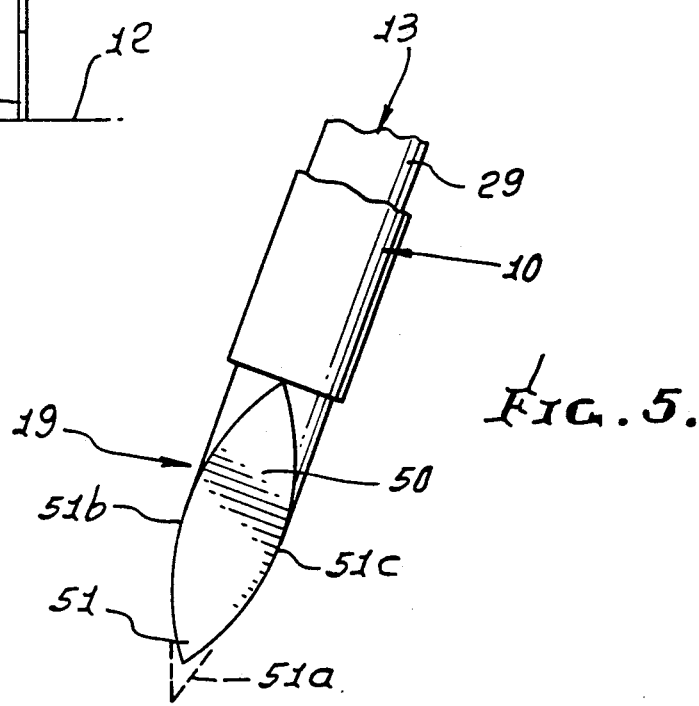

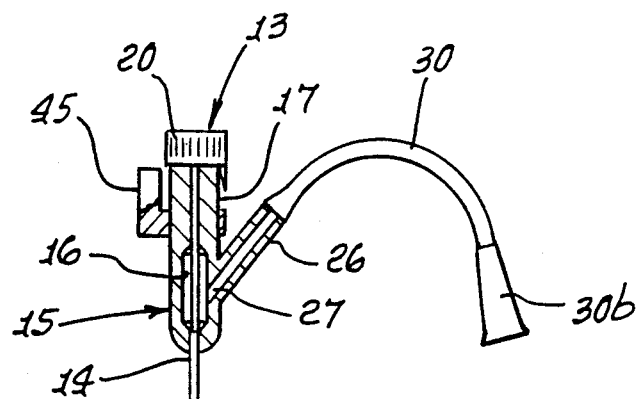
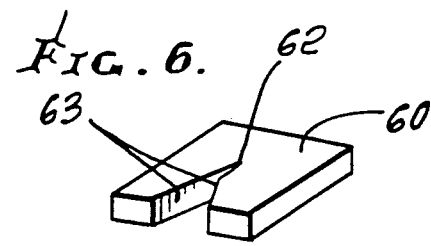
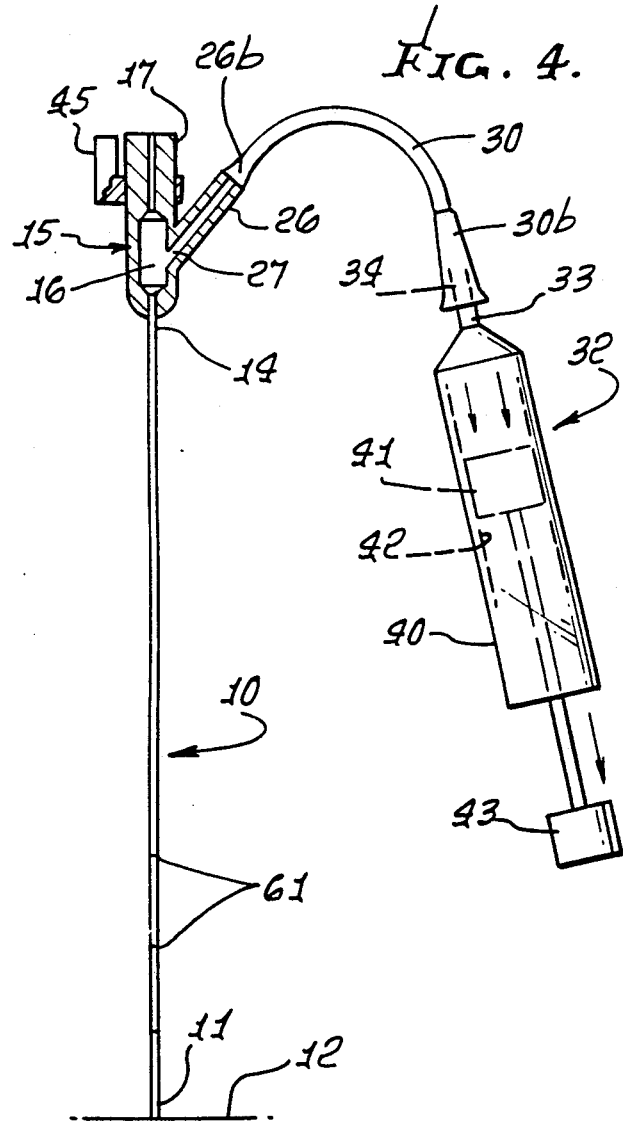
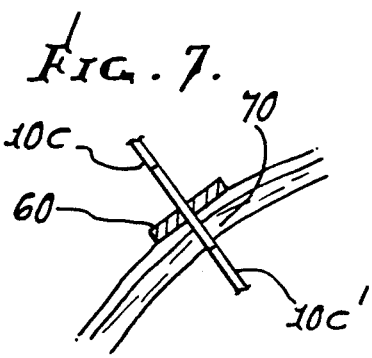

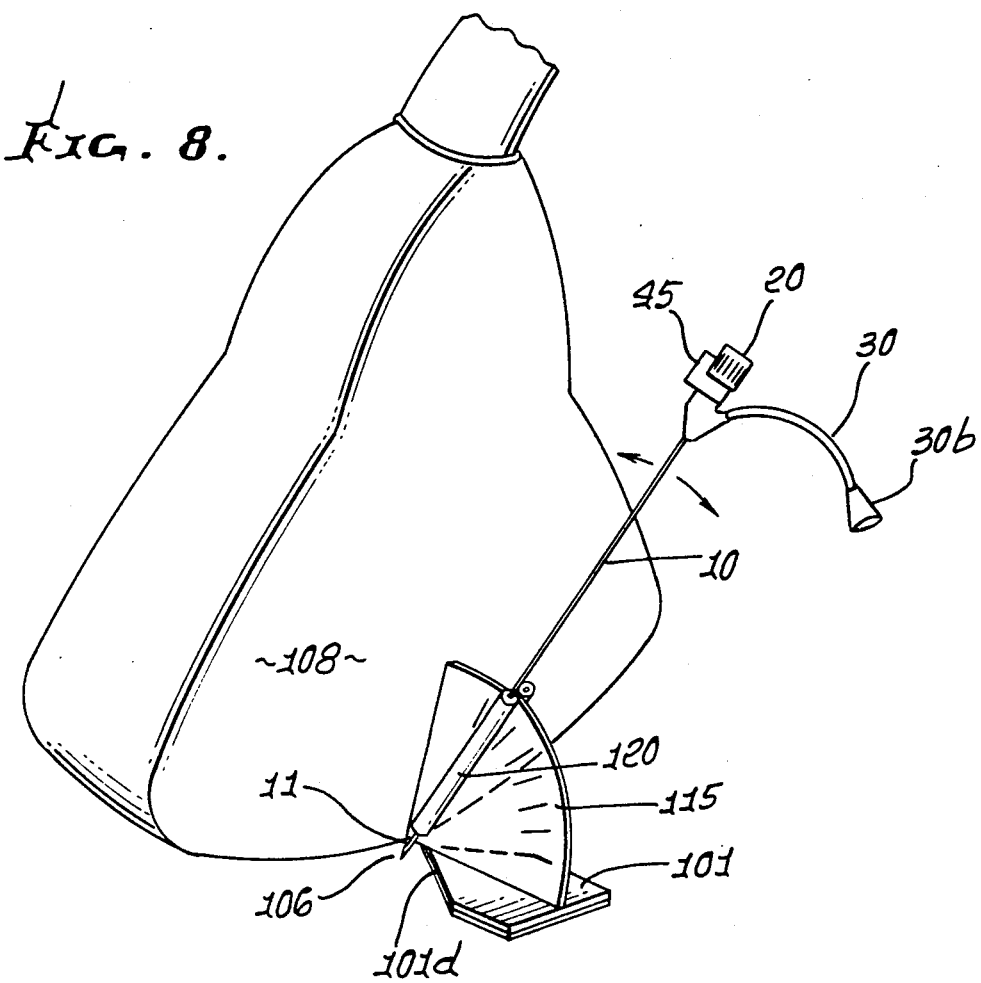
Fig. 8.
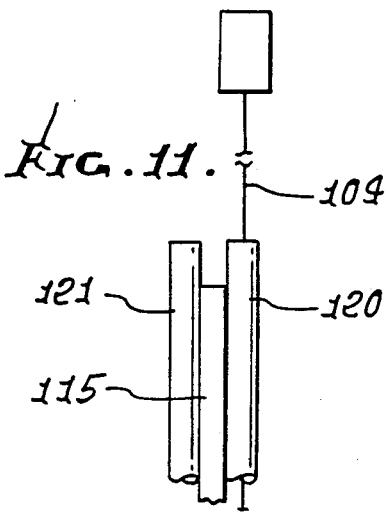
Fig. 11.
Fig. 12.

1

DISPOSABLE UNIVERSAL NEEDLE GUIDE APPARATUS (FOR AMNIOCENTESIS)

This application is a continuation-in-part of Ser. No. 546,896 filed July 2, 1990, now U.S. Pat. No. 5,069,665.

BACKGROUND OF THE INVENTION

This invention relates generally to amniocentesis procedures, and more particularly to apparatus and techniques enhancing the accuracy and safety of such procedures.

Amniocentesis is an obstetrical procedure in which a small gauge needle is inserted percutaneously through the uterus into the pregnancy sac to obtain a sample of the amniotic fluid for prenatal genetic and biochemical studies. In order to reduce the possibility of needle injuries to the placenta and the fetus, this invasive procedure is performed under direct vision techniques using ultrasound, as the needle is being inserted through the tissue layers into the pregnancy sac. Both free hand insertion and techniques employing needle guides are presently used. Needle guides are designed to increase the accuracy of the insertion as compared to the free hand technique.

Presently used needle guides are constructed as parts of transducer probes, and because of such attachment, much of the desired maneuverability is lost. An "articulated" needle guide has been described recently (OB-GYN, Vol. 74, No., 1989), but it still has to be attached to the transducer probe itself and thereby offers no maneuverability advantage. Besides, due to the employment of a large number of moving parts (and joints) in this needle guide, the design has defeated its purpose by unnecessarily requiring a large number of variables that need to be adjusted and fixed to properly position the needle, thereby increasing the chance of inaccuracy in setting the needle direction. This also produces considerable clumsiness in its overall application.

SUMMARY OF THE INVENTION

It is a major object of the invention to provide a simple and effective surgical needle guide apparatus which affords extreme maneuverability of the needle being inserted, and enables accurate needle positioning independently of an ultrasound transducer, thereby enhancing safety. Basically, the apparatus includes:

a) a substantially horizontal base to be applied to a surface on or adjacent a patient's body surface zone to be punctured by the needle, b) an upright guide flange mounted on the base, there being pivot means associated with the flange and base and projecting beyond the base, to overhang an open zone adjacent the surface and offset from the flange, c) and elongated, tubular guide means having a lower end portion carried by the pivot means to be manually pivoted so that the needle means swings adjacent the guide flange, the tubular means adapted to receive needle means for guiding movement thereof toward the open zone and at an angle determined by selective swinging of the tubular guide means relative to the base.

As will be seen, the upright flange may advantageously have a lower end overhang portion overhanging the open zone, and the pivot means is located in the overhang portion of the flange; also, the flange may have the general form of a quadrant, with an upright forward edge, and a convexly curved edge extending from the top of the upright formed edge rearwardly and downwardly to the base. That quadrant-shaped flange may also have angularly spaced position indicating indicia thereon, associated with the curved edge, to indicate the selected angularity of the tubular guide means relative to horizontal.

The needle means typically comprises a needle having a tip at the open zone, and a shank in the tubular guide means; and the latter may include parallel guide tubes respectively at opposite sides of the guide flange, the tubes interconnected to be swung together.

Further, adhesive means may be provided on the base to enable rapid and accurate adhesion of the base to a selected surface in the patient's body.

The needle itself may comprise an aspiration needle assembly that includes a) a linearly elongated, tubular needle having a first end to be positioned at or proximate a patient's body, and an opposite end portion, b) a hub integral with the opposite end portion of the needle and providing a reservoir, the hub having a first duct in linear communication with the needle via the reservoir, and there being a second duct in communication with the reservoir and branching relatively away from the first duct, the second duct connected to the hub, c) the first duct, reservoir and needle being in linear alignment to receive an elongated stylet having a sharp end, and manipulable to cause the sharp end to penetrate the patient's body, and to be withdrawn so that body fluid can pass through the needle and enter the reservoir, d) and flexible, coupler tubing operatively connected to the second duct for passing fluid between the reservoir and a syringe operatively connected to the reservoir via the flexible tubing, whereby the syringe may be bodily manipulated in force-transmitting relation isolation relative to the needle.

As will be seen, the hub and ducts are typically integral, with the ducts extending in Y-shaped relative configuration; and a stopper is typically associated with the first duct and manipulable to close the first duct after withdrawal of the stylet from the needle.

These and other objects and advantages of the invention, as well as the details of an illustrative embodiment, will be more fully understood from the following specification and drawings in which:

DRAWING DESCRIPTION

FIG. 1 is a side elevation showing a needle and associated hub and ducts, and flexible branch tubing;

FIG. 2 is an elevation showing a stylet to be received in the needle;

FIG. 3 shows the stylet inserted into the needle to produce a body puncture;

FIG. 4 is a view like FIG. 1 showing a syringe attached to the flexible branch tubing;

FIG. 5 is an enlarged fragmentary side view of a terminal portion of the stylet;

FIG. 6 is a perspective view of a flat marker plate;

FIG. 7 is a section showing use of the marker plate on a needle;

FIG. 8 is a perspective view showing the pivoted, tubular guide assembly;

Figure 9:
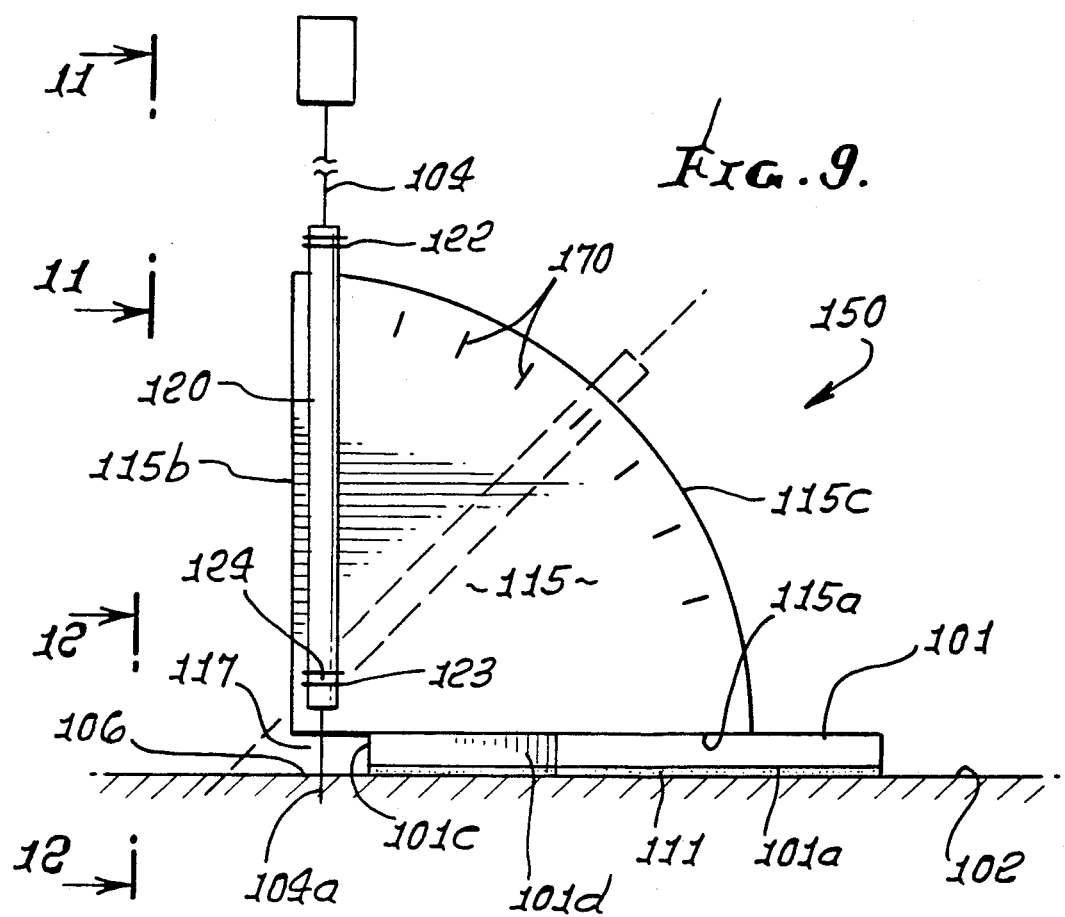
FIG. 9 is an enlarged side elevation of the tubular guide assembly.
Figure 10:
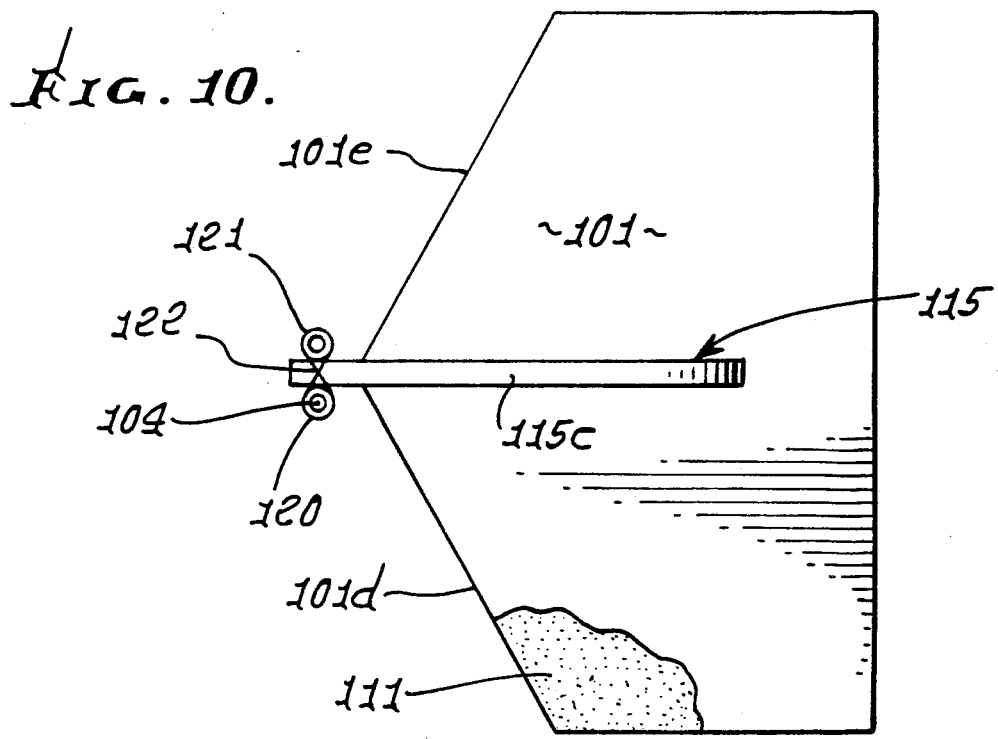
FIG. 10 is a top plan view of the FIG. 9 assembly.

FIGS. 11 and 12 are fragmentary elevations taken on lines 11—11 and 12—12, respectively, of FIG. 9.

DETAILED DESCRIPTION

Referring first to FIGS. 7–12, guide apparatus 150 includes a substantially horizontal base plate 101 to be applied to a surface 102 on or adjacent to a patient's body surface zone 106 to be punctured by a needle 104. The latter has a tip 104a controllably positioned just above the zone 106, for example immediately above a pregnancy sac in the patient's uterus. Zone 106 may be located or determined by an ultrasound transducer 108, as seen in FIG. 8, and is typically marked so that the needle can be aimed at the target zone 106. The angle of entry of the needle is then to be fixed and the needle accurately maintained in position and at selected angularity, irrespective of the transducer.

For this purpose, the base plate 101 is then adhered to the patient's body, or to surface 102, and to this end an adhesive layer of strip 111 may be carried at the underside 101a of plate 101, as seen in FIG. 9, to affix the plate in position with the needle tip just above target zone 106.

Also an upright guide flange 115 is fixedly mounted on the base, i.e. horizontal lower edge 115a of the flange may be attached to or integral with the base.

Pivot means is associated with the flange and base, and projects beyond the base to overhang the open space or zone 117 just above target zone 106, space 117 being offset from the edge 101c of the base. Note also base edges 101d and 101e in FIG. 10 tapered forwardly, i.e., aimed toward zone 117 to assist in base and needle placement. The flange 115 is shown to have an upright, i.e., vertical forward edge 115b, which may be initially aligned adjacent the surface of the transducer.

The apparatus also includes elongated tubular guide means having a lower end portion carried by the pivot means to be manually pivoted so that the needle means swings adjacent the guide flange, the tubular means adapted to receive needle means for guiding movement thereof toward the open zone and at an angle determined by selective swinging of the tubular guide means relative to the base.

In the example, the tubular guide means comprises two parallel guide tubes (transparent plastic, for example) 120 and 121, which are carried at opposite sides of the flange 115, which itself may consist of transparent plastic. Tubes 120 and 121 in upright position are near edge 115b. Note the attachment means in the form of connector wires 122 extending about the two tubes at an upper elevation, and connector wires 123 extending about the two tubes at a lower elevation. Such lower wire or wires 123 may pass through the plate to provide the lower pivot means at 124 to pivot the tubes to the plate, to be swung as referred to. A needle 104 is shown selectively received in one of the tubes for accurate placement relative to the body zone to be punctured. The needle has a shaft selectively inserted into one of the tubes, the needle and tubes extending at a selected angle relative to horizontal. Note needle tip 104a. The two tubes 120 and 121 may frictionally engage opposite sides of the plate to be lightly held in selected angular position. All of such structure is readily disposable after use.

Note curved, circular edge 115c of the flange 115 in the form of a quadrant edge, and like a protracter, with indicia at 170 at angular intervals to allow selective positioning of the tubular guides, aligning with the indicia, thereby to accurately locate the puncture needle, angularly.

The needle may otherwise take the form of a tubular fluid aspiration needle 10, as also seen in FIGS. 1–7 and 8, that needle being linearly elongated and having a lower, i.e., first, end 11 to be positioned at or proximate a patient's body 12, to enter a wound or puncture produced by tip 51 of a stylet 13. The opposite end portion 14 of the needle is integral with a hub 15, which is enlarged and tubular, to form a reservoir 16. The hub includes an integral first duct 17 in linear communication with the needle, via the reservoir, so that the stylet can be passed through the bore 18 of the duct 17, then through the reservoir, and into and through the needle to puncture the body as seen in FIG. 3.

The stylet 13 includes an elongated, narrow, cylindrical shaft 29, sharpened at its lower end portion 19. A flange 20 at the upper end of the stylet is manually manipulable to insert the stylet in the needle hub 15, and it is downwardly engageable with the upper end 17a of the first duct to limit downward displacement of the stylet sharpened lower end relative to the needle. The lower end 11 of the needle is blunt, to rest against the body surface 12 during stylet manipulation, but the needle is thin-walled to permit its travel into the wound produced by the stylet, for fluid aspiration.

As seen in the drawings, a second duct 26 is also in communication with the reservoir, at its side (see location 27); and the second duct is connected with the side of the hub to branch away from the hub, in Y-shaped relation with the first duct. Both ducts are typically formed of rigid plastic material, as is the hub; but they could consist of other material, such as metal. Flexible tubing 30 is operatively connected to the end 26b of the second duct for passing body fluid collecting in the reservoir to a syringe 32 seen in FIG. 4. While that syringe has a tube 33 suitably removably connected at 34 to a flared wall portion 30b of the tubing 30, manual manipulation and displacement of the syringe during its use creates force that is not transmitted to the needle, due to flexing of the coupler tubing 30. This feature is important, since endwise or lateral displacement of the needle, while it is in the wound or puncture formed by the stylet, could be dangerous, as for example to a fetus during amniocentesis. The syringe includes the usual cylinder 40, plunger 41 in chamber 42, and handle 43.

In use the stylet is withdrawn from the wound and may be withdrawn from the needle during insertion of the needle into the wound, and to desired depth. The first duct 17 is closed, after removal of the stylet, as by rotation of a stopper 45 to close the bore of 17. The needle is then pushed into the body, via the wound. The syringe is then attached to 30b and used to draw liquid from the body via reservoir 16. The syringe is then detached, and the needle withdrawn.

FIG. 5 shows the cylindrical stylet lower end as sharpened due to forming of a side flat 50 angled to taper from one side of the stylet toward the other, and endwise toward tip 51. The sharp, tapered tip 51 may be slightly dulled or blunted, as from a more sharp condition, indicated by broken lines 51a, formed when flat 50 is ground. The sharp, lateral edges 51b and 51c of the flat may also be slightly dubbed for safety.

FIGS. 6 and 7 show use of a flat plate marker 60, adjustably positioned on the needle shank 10c and held in position by friction at selected "depth" (needle penetration) position, indicated by notches or other indicators 61 on the shank. The flat plate has an undersized opening 62 to pass the needle, but also to grip it, frictionally. A side fissure 63 in the plate is tapered as shown, and allows relative movement of the needle shank sidewardly into through opening 62, the shank tending to slightly spread the opening to provide friction.

FIG. 7 shows the needle shank extent 10c', below the marker, penetrating the body at 70. The plate flatly engages the body outer skin surface to limit needle penetration.

The needle assembly, as described, may be suitably disposed of after use.

Referring back to FIGS. 9-12, distinct advantages are:

1. Once the site of needle entry has been determined by ultrasound scanning prior to the start of the procedure, the new needle guide is foam taped onto the skin at the site of puncture and remains completely unattached to the probe. In this way, the ultrasound probe can be easily manipulated to obtain the clearest visibility of the needle during insertion without any interference of the needle at all.

2. By its design, the new needle guide reduces all variables in setting the direction of the needle path to a single plane, i.e., a perpendicular plane to the body surface at the site of entry.

3. In this single perpendicular plane to the base plate, the needle is mounted into a needle channel which can be rotated from a vertical direction up to a 90° angle of entry at the skin surface.

4. The double-channel symmetrical design allows the guide to be fixed on both left and right sides of the midline of the abdomen.

5. The upright plate employs a straight, vertical edge that can be directly opposed to the transducer probe for better needle visualization during insertion; a distinct advantage over the presently used guides which lack such close and direct application.

6. By functioning independently of the various ultrasound transducer probes, the invention is completely compatible with any size, shape or design of probes presently available.

I claim:

1. In surgical guide apparatus for needle means, the combination comprising:
 a) a substantially horizontal base to be applied to a surface on or adjacent a patient's body surface zone to be punctured by the needle means,
 b) an upright guide flange mounted on the base, there being pivot means associated with the flange and base and projecting beyond the base, to overhang an open zone adjacent said surface and offset from the flange,
 c) elongated, tubular guide means having a lower end portion carried by said pivot means to be manually pivoted so that the needle means swings adjacent the guide flange, said tubular means adapted to receive said needle means for guiding movement thereof toward said open zone and at an angle determined by selective swinging of the tubular guide means relative to the base,
 d) said needle means being in the form of a linearly elongated tubular needle, having a first end to be positioned at or proximate a patient's body, and an opposite end portion,
 e) a hub integral with said opposite end portion of the needle and providing a reservoir, the hub having a first duct in linear communication with the needle via said reservoir, and there being a second duct in communication with the reservoir and branching relatively away from the first duct, the second duct connected to the hub, said hub being enlarged relative to the needle,
 f) the first duct, reservoir and needle being in linear alignment to receive an elongated stylet having a sharp end, and manipulable to cause said sharp end to penetrate the patient's body, and to be withdrawn so that body fluid can pass through the needle and enter the reservoir,
 g) and flexible, coupler tubing operatively connected to said second duct for passing fluid between the reservoir and a syringe operatively connected to said reservoir via said flexible tubing, whereby the syringe may be bodily manipulated in force-transmitting relation isolation relative to the needle.

2. The combination of claim 1 wherein said flange has a lower end overhang portion overhanging said open zone, and said pivot means is located in said overhang portion of the flange.

3. The combination of claim 2 including adhesive means on said base to adhere the base to a selected surface area on the patient's body.

4. The combination of claim 1 wherein said flange has the general form of a quadrant, with an upright forward edge, and a convexly curved edge extending from the top of said upright forward edge rearwardly and downwardly to said base.

5. The combination of claim 4 wherein said quadrant-shape flange has angularly spaced position indicating indicia thereon, associated with said curved edge, to indicate the selected angularity of said tubular guide means relative to horizontal.

6. The combination of claim 4 including said needle means guidedly received in said tubular guide means, and having tip means at said zone.

7. The combination of claim 1 including said needle means guidedly received in said tubular guide means and having tip means at said zone.

8. The combination of claim 1 including adhesive means on said base to adhere the base to a selected surface area on the patient's body.

9. The combination of claim 1 wherein said hub is enlarged relative to the needle.

10. In surgical guide apparatus for needle means, the combination comprising:
 a) a substantially horizontal base to be applied to a surface on or adjacent a patient's body surface zone to be punctured by the needle means,
 b) an upright guide flange mounted on the base, there being pivot means associated with the flange and base and projecting beyond the base, to overhang an open zone adjacent said surface and offset from the flange,
 c) elongated, tubular guide means having a lower end portion carried by said pivot means to be manually pivoted so that the needle means swings adjacent the guide flange, said tubular means adapted to receive said needle means for guiding movement thereof toward said open zone and at an angle determined by selective swinging of the tubular guide means relative to the base,
 d) and wherein said tubular guide includes two parallel guide tubes respectively at opposite sides of said guide flange, said tubes interconnected to be swung together.

11. The combination of claim 10 including said needle means that comprises an elongated needle having a shaft selectively inserted into one of said tubes, said needle and tubes extending at a selected angle relative to horizontal.

12. In surgical guide apparatus for needle means, the combination comprising:
   a) a substantially horizontal base to be applied to a surface on or adjacent a patient's body surface zone to be punctured by the needle means,
   b) an upright guide flange mounted on the base, there being pivot means associated with the flange and base and projecting beyond the base, to overhang an open zone adjacent said surface and offset from the flange,
   c) elongated, tubular guide means having a lower end portion carried by said pivot means to be manually pivoted so that the needle means swings adjacent the guide flange, said tubular means adapted to receive said needle means for guiding movement thereof toward said open zone and at an angle determined by selective swinging of the tubular guide means relative to the base,
   d) said flange having the general form of a quadrant, with an upright forward edge, and a convexly curved edge extending from the top of said upright forward edge rearwardly and downwardly to said base,
   e) said quadrant-shape flange has angularly spaced position indicating indicia thereon, associated with said curved edge, to indicate the selected angularity of said tubular guide means relative to horizontal,
   f) said needle means being in the form of a linearly elongated tubular needle, having a first end to be positioned at or proximate a patient's body, and an opposite end portion,
   g) a hub integral with said opposite end portion of the needle and providing a reservoir, the hub having a first duct in linear communication with the needle via said reservoir, and there being a second duct in communication with the reservoir and branching relatively away from the first duct, the second duct connected to the hub,
   h) the first duct, reservoir and needle being in linear alignment to receive an elongated stylet having a sharp end, and manipulable to cause said sharp end to penetrate the patient's body, and to be withdrawn so that body fluid can pass through the needle and enter the reservoir,
   i) and flexible, coupler tubing operatively connected to said second duct for passing fluid between the reservoir and a syringe operatively connected to said reservoir via said flexible tubing, whereby the syringe may be bodily manipulated in force-transmitting relation isolation relative to the needle.

13. The combination of claim 12 wherein said hub, and said first and second ducts are integral, the ducts having Y-shaped relative configuration.

14. The combination of claim 12 including a stopper associated with the first duct and manipulable to close the first duct after withdrawal of the stylet from the needle.

15. The combination of claim 12 including said stylet inserted into and extending within the needle, the stylet having a first end portion protruding from the needle to penetrate the patient's body.

16. The combination of claim 12 wherein the stylet is cylindrical and longitudinally and axially elongated, and said first end portion thereof defines a side flat that tapers from on side of said end portion toward the other side thereof 17. The combination of claim 16 wherein said flat terminates at a tapered tip and the flat has edges extending toward said tip, at least one of said tip and edges being dubbed to reduce the sharpness thereof.

18. The combination of claim 12 including said syringe attached to said flexible tubing, in spaced relation to the needle and hub.

19. The combination of claim 12 including a marker body removably and frictionally attached to the needle, and adjustable along the needle length to a selected position to indicate depth of needle penetration into the patient's body.

20. The combination of claim 19 wherein said marker body is a plate having an opening therethrough to pass the needle, and also having a through fissure extending from the plate edge to said opening to pass the needle sidewardly relative to the marker body and into said opening, for use on the needle.

* * * * *